United States Patent [19]

Gough

[11] Patent Number: 4,890,620
[45] Date of Patent: *Jan. 2, 1990

[54] TWO-DIMENSIONAL DIFFUSION GLUCOSE SUBSTRATE SENSING ELECTRODE

[75] Inventor: David A. Gough, Cardiff by the Sea, Calif.

[73] Assignee: The Regents of the University of California, Berkeley, Calif.

[*] Notice: The portion of the term of this patent subsequent to Mar. 17, 2004 has been disclaimed.

[21] Appl. No.: 161,214

[22] Filed: Feb. 17, 1988

Related U.S. Application Data

[63] Continuation of Ser. No. 79,169, Jul. 28, 1987, abandoned, which is a continuation of Ser. No. 778,061, Sep. 20, 1985, abandoned.

[51] Int. Cl.$^4$ .............................................. A61B 5/00
[52] U.S. Cl. ..................................... 128/635; 204/403; 204/415
[58] Field of Search ................ 128/635; 204/403, 415, 204/431, 432

[56] References Cited

U.S. PATENT DOCUMENTS

| | | | |
|---|---|---|---|
| 3,542,662 | 11/1970 | Hicks et al. | 204/403 |
| 3,948,745 | 4/1976 | Guilbault et al. | 204/195 B |
| 3,979,274 | 9/1976 | Newman | 204/195 B |
| 4,252,123 | 2/1981 | Kimmich | 128/635 |
| 4,431,004 | 2/1984 | Bessman et al. | 128/635 |
| 4,431,507 | 2/1984 | Nankai et al. | 204/403 |
| 4,458,686 | 7/1984 | Clark, Jr. | 128/635 |
| 4,492,622 | 1/1985 | Kuypers | 128/635 |
| 4,650,547 | 3/1987 | Gough | 204/403 X |

FOREIGN PATENT DOCUMENTS 1152155 8/1983 Canada .
0169668 10/1982 Japan .................................. 128/635

OTHER PUBLICATIONS

Fischer et al, "A Membrane . . . Biological Fluids", Trans Am Soc Artif Inter Organs, vol. 28, 1982, pp. 245-248.
"Nylon Shavings Enzyme Reactor for Batch Determination of Urea", by Kazi D. Begum and Horacio A. Mottola, Analytical Biochemistry 142, 1-6 (1984), pp. 1-3.
"Progress Toward a Potentially Implantable, Enzyme-Based Glucose Sensor", by Gough et al., Diabetes Care, vol. 5, No. 3, May-Jun. 1982, Part 1, pp. 190-198.
"Electrode-Based Enzyme Immunoassays Using Urease Conjugates", by Meyerhoff et al., Analytical Biochemistry 95, 483-493 (1979), pp. 483-484.
"The Enzyme Electrode", by S. J. Updike and G. P. Hicks, Nature, vol. 214, Jun. 3, 1967, pp. 986-988.

Primary Examiner—Lee S. Cohen
Attorney, Agent, or Firm—Brown, Martin, Haller & McClain

[57] ABSTRACT

Enzyme electrode assembly suitable for sensing physiologically important molecules such as glucose wherein the rate of accessibility of enzyme substrates to the enzyme is differentially regulated by suitably positioning material with selective permeability properties around the sensing region of the electrode assembly.

25 Claims, 2 Drawing Sheets

TWO-DIMENSIONAL DIFFUSION GLUCOSE SUBSTRATE SENSING ELECTRODE

This is a continuation of application Ser. No. 079,169, filed July 28, 1987, now abandoned, which is a continuation of Ser. No. 778,061 filed Sep. 20, 1985, now abandoned.

BACKGROUND OF THE INVENTION

It is a standard practice to treat diabetes mellitus predominately with injections of insulin to counter the inability of the pancreas to manufacture and secrete insulin in response to elevated blood glucose levels. For optimal therapy, it is necessary to determine the glucose concentration in the body in order to specify the appropriate amount and time of the antidiabetes medication. This requires a glucose sensing device, which may be most effective if implanted in the body.

One approach to the development of an implantable sensor is the so-called enzyme electrode in which an immobilized enzyme catalyzes a chemical reaction between glucose and another molecule such as oxygen that can be detected by an electrode. The enzymatic reaction is one in which glucose is catalytically converted to gluconic acid with the simultaneous consumption of oxygen promoted by the enzyme glucose oxidase, with the resulting decrease in oxygen determined by an amperometric oxygen electrode and thereby related to glucose levels. A key problem in developing this sensor is that the glucose concentration in the body is normally higher than the oxygen concentration by a factor of 50–1000 times. Thus, since the enzymatic reaction is limited by oxygen, the least abundant reactant, glucose measurements in the body are often inaccurate. Most previous investigators have not recognized or gone beyond this problem.

Hicks et al. in U.S. Pat. No. 3,542,662 describe an electrolytic glucose sensor capable of assaying glucose in fluid removed from the body, but not usable for measuring glucose directly in vivo. Hicks et al. describe an enzyme-containing membrane disposed between a fluid being assayed and first oxygen sensor electrode and a similar membrane not containing enzymes disposed between a fluid and second reference oxygen electrode. Oxygen diffuses through the enzyme-containing membrane and is consumed in an equal molar reaction with glucose catalyzed by the enzyme glucose oxidase; consequently, oxygen is unavailable for detection by the oxygen sensor electrode. The second oxygen sensor electrode measures the concentration of oxygen existing absent any enzyme-catalyzed reaction. The difference in oxygen levels detected by the two electrodes is proportional to the glucose concentration within certain limits.

The glucose sensor described by Hicks et al. performs satisfactorily when assaying for glucose in vitro. However, when the sensor is used directly in the body, its performance is unreliable. In part, this appears to be due to the inability of the dual-sensor design to function adequately in low-oxygen environments.

Presently there does not exist an implantable sensor suitable for detecting glucose in regions of the body where oxygen concentrations are lower than glucose concentrations. Previously, however, Fisher and Abel in "A Membrane Combination for Implantable Glucose Sensors, Measurements in Undiluted Biological Fluids" (*Trans. Am. Soc. Artif. Intern. Organs,* Vol. XXVIII, 1982) have attempted to solve the problem by positioning sandwich membrane in association with an oxygen electrode sensor. The membranes consist of a hydrophobic layer over an enzyme layer, with the former having a minute hole aligned with the oxygen electrode sensor so as to allow predominately access of glucose from the fluid being assayed. The hydrophobic layer was selected to be permeable predominantly to oxygen; consequently, oxygen diffused into the enzyme layer at all points across the surface of the hydrophobic layer whereas glucose diffused in only at the region of the hole. In this manner, a stoichiometric excess of oxygen over glucose was provided to the enzyme layer. As a result of the requirement that glucose entry be restricted to a small opening in the hydrophobic membrane, this oxygen electrode sensor apparatus is limited as to the range of concentrations of glucose detectable. Also, because the enzyme situated near the opening in the hydrophobic membrane is constantly exposed to incoming glucose, it tends to become inactivated, which in turn requires that for the sensor to continue functioning glucose must diffuse further into the membrane, which additionally limits the use of the sensor in that it increases its response time.

BRIEF SUMMARY OF THE INVENTION

An oxygen electrode sensor is described that can be implanted in the body, and which is suitable for detecting glucose in regions of the body where oxygen concentrations are stoichiometrically less than glucose concentrations. The sensor consists of a hydrophilic layer containing enzyme in communication with the sensor and a hydrophobic layer in communication with the hydrophilic layer. The hydrophilic and hydrophobic layers are positioned so that the enzyme substrates, glucose and oxygen diffuse predominantly in a two-directional manner such that the substrates enter the hydrophilic layer at right angles to each other. Oxygen enters the enzyme region by diffusion through the hydrophobic layer and, to a lesser extent, through the exposed surface of the hydrophilic layer; but glucose, being incapable of diffusion in the hydrophobic layer, enters only through the exposed surface of the hydrophilic layer. By establishing a two-directional diffusion gradient of substrates, it is possible to effectively increase the relative oxygen concentration entering the enzyme region. Additionally, a second oxygen sensor electrode capable of acting as a reference electrode to measure the level of ambient oxygen present in the absence of enzymatic catalysis of glucose is described.

BRIEF DESCRIPTION OF THE DRAWINGS

Reference is made to the drawings illustrating various embodiments of the invention in which.

DETAILED DISCLOSURE OF THE INVENTION

Figure 1:
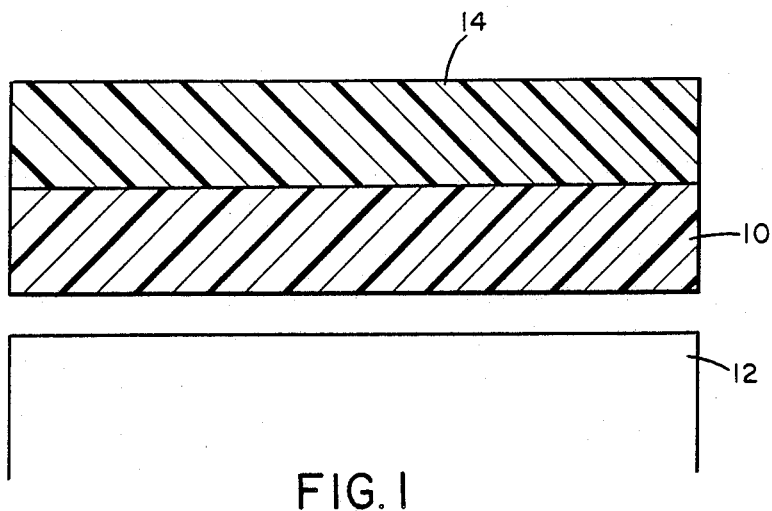
FIG. 1 is a schematic diagram of one form of the present invention.

The invention will be described as applied to determining concentrations of glucose in bodily fluids containing a large stoichiometric excess of glucose over oxygen. It will be understood, however, by those skilled in the arts that the electrode assembly of the present invention is not limited to assay solely glucose, and that it may be used to assay other molecules such as amino acids, lactates, alcohols, or similar molecules commonly found in bodily fluids that are substrates for oxidase enzymes that require the presence of a gaseous species to undergo enzymatic conversion.

An electrode assembly suitable for detecting concentrations of glucose in bodily fluids where the electrode assembly detects a change in oxygen due to the conversion of glucose to gluconic acid is constructed of three parts: an electrochemical oxygen sensor having the appropriate geometry, a gelatinous layer made of hydrophilic material, and a hydrophobic layer. The gelatinous hydrophilic material contacts the sensor part of the assembly. Contained within, or associated with, the gelatinous material is a enzyme, glucose oxidase, and optionally a second enzyme, catalase. The oxidase enzyme promotes the following reaction:

glucose+oxygen+water→gluconic acid+hydrogen peroxide

Hydrogen peroxide can be decomposed by incorporating catalase in the gelatinous material should it be desirable to do so. Catalase catalyzes the following reaction:

$H_2O_2 \rightarrow \tfrac{1}{2}O_2 + H_2O$

Materials useful for preparing the gelatinous layer include polyacrylamide gels, glutaraldehyde - cross-linked collagen or albumin, polyhydroxyethylmethacrylate and its derivatives and other hydrophilic polymers and copolymers. The layer can similarly be constructed by cross-linking glucose oxidase or other enzymes with chemical cross-linking reagents.

In association with the gelatinous hydrophilic layer is a second layer made of hydrophobic material. Materials suitable for constructing the second layer are polydimethylsiloxane, polymers of tetrafluoroethylene or its fluorochloro analogs alone or as copolymers with ethylene or propylene, polyethylene, polypropylene, cellulose acetate, and other oxygen-imbibing polymeric materials. Generally, these materials will account for about 2%–40% of the combined weight of the hydrophilic and hydrophobic layers.

The hydrophilic gel layer containing the enzyme will most often be disposed between a thin layer of the hydrophobic material covering a portion or all of the face of the hydrophilic layer and the oxygen sensor but leaving the edge surfaces, due to the thickness of that layer, accessible to the solution to be analyzed. The hydrophilic gelatinous layer is permeable to both glucose and gaseous molecules, such as oxygen. Glucose oxidase impregnated in the hydrophilic layer acts on glucose and oxygen as they diffuse through it.

The hydrophobic material of the second layer is relatively impermeable to glucose but permeable to oxygen. Since the conversion of glucose to gluconic acid is limited stoichiometrically by whichever component is present at the oxygen-sensitive electrode in lowest concentration, in order to make the electrode assembly sensitive to glucose concentrations oxygen within the enzyme region must be at least stoichiometrically equal to glucose. This requirement is met by covering the hydrophilic gel layer with the hydrophobic layer, which hinders the rate of entry of glucose but provides access of oxygen to the gel layer. Thus, disposing the hydrophobic layer in a body or bodies that limits the surface area of the hydrophilic gel layer exposed for accepting glucose from bodily fluids causes a reduced rate of entry of glucose into the hydrophilic gel layer, which decreases the concentration of glucose inside the hydrophilic gelatinous layer to a concentration that allows for stoichiometric reaction with oxygen.

In order to efficaciously measure glucose in low oxygen concentrations in the body, the first and second layers of the electrode assembly, hydrophilic and hydrophobic layers, respectively, can be positioned relative to each other in several ways. In the electrode assembly shown in FIG. 1, glucose enters the membrane only through the edge surfaces of the gelatinous hydrophilic layer 10 and diffuses toward the center portion of the layer substantially parallel to the face of the surface of the layer and the surface of the planar sensor 12. The gaseous species, oxygen, enters the hydrophobic membrane 14 through the entire exposed surface of the hydrophobic layer and subsequently penetrates into the gelatinous hydrophilic layer to insure that there is an excess of oxygen over glucose.

Figure 2:
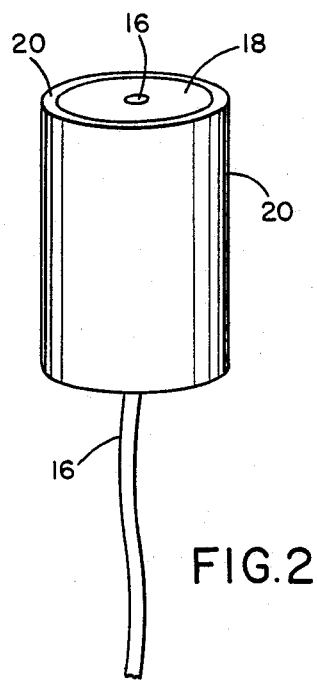
FIG. 2 is a schematic presentation of a second form of the present invention.

An additional configuration of the hydrophilic and hydrophobic layers is shown in FIG. 2. Here the oxygen sensor portion 16 of the assembly exhibits a cylindrical shape with its active surface being the curve of cylindrical face rather than the flat end. A concentric hydrophilic layer 18 contains the enzymes that contacts the oxygen sensor portion along the curved surface and a concentric hydrophobic layer 20 contacts the curved face but not the flat face of the hydrophilic layer. In this arrangement, the glucose enters only through the flat hydrophilic exposed edge and oxygen enters predominantly through the curved sides of the hydrophobic layer.

Figure 3:
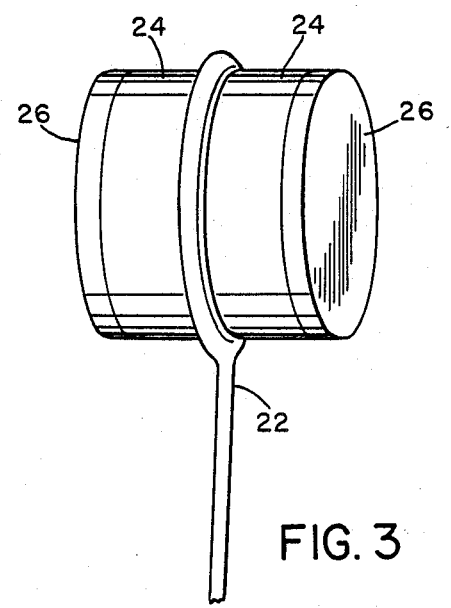
FIG. 3 is a still further form schematically representing the present invention.

A third arrangement shown in FIG. 3 is a combination of a circular-plate oxygen sensor 22 sensitive to oxygen on one or both of its flat surfaces but not at the curved edges, with a hydrophilic enzyme-containing layer 24 contacting the oxygen sensor on each side and with a hydrophobic layer 26 contacting the outer surface of each hydrophilic layer but not the circular edge. Thus, oxygen predominantly enters from both sides through the two hydrophilic layers in a direction perpendicular to the plane while glucose enters only through the hydrophilic circumferential edge.

Figure 4:
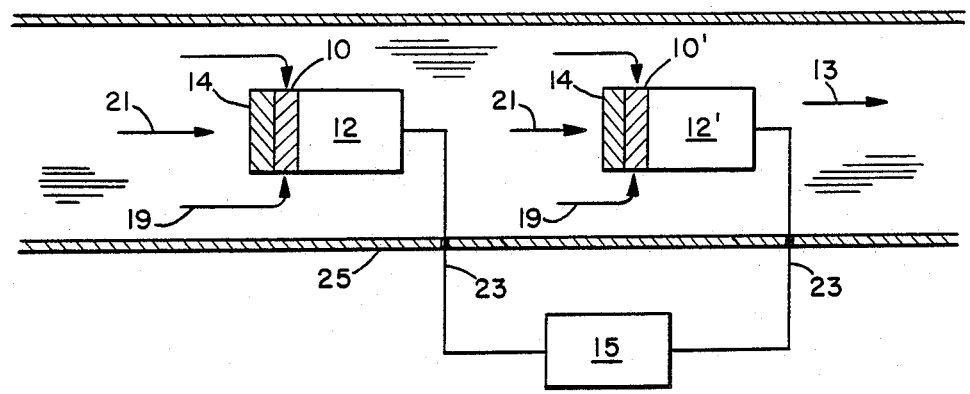
FIG. 4 is a schematic diagram illustrating the present system positioned to measure concentration of a component in a bodily fluid.

The overall system is illustrated schematically in FIG. 4. Each of the sensors 12 is disposed in the bodily fluid, in this case shown schematically as confined in conduit 25. The fluid is shown flowing in the direction indicated by arrow 13 and encountering layers 10 and 14 ahead of each of the sensors 12. One of the sensors 12 (here designated 12') is the sensor in which the first layer 10 contains the catalyst or enzyme; in this Figure that layer is designated 10'. The first material in the fluid cannot flow through the layer 14 and therefore must enter the layer 10 (or 10') through its periphery as indicated by arrows 19. The second material in the bodily fluid 17 can penetrate both layers 10 and 14 and therefore flows through not only through the periphery as indicated by arrow 19 but also through the face of each layer as indicated by arrow 21. The signals generated by the sensors 12 are carried through transmission lines 23 to comparing means 15 which incorporates appropriate devices such as meters, charts or the like to provide a visual and/or written record of the concentration of the first material as determined from the comparison of the two signals.

To insure operation of the sensor assembly to respond to glucose at low relative external concentrations of oxygen, the hydrophilic layer containing glucose oxidase is designed so that oxygen passes readily into it through the exposed edge and through the contacting hydrophobic layer whereas glucose, diffuses into it only through the exposed edge and not through the hydrophobic layer. The ratio of oxygen to glucose is thus controlled by (1) the external concentrations, (2) the entry and/or transport properties of the combination of hydrophilic and hydrophobic layers, and (3) the aspect ratio, or ratio of the area of the exposed hydrophilic surface available for glucose transport to the area of the hydrophobic surface available to only oxygen transport. The relative proportions of glucose and oxygen are thus changed from a concentration ratio in the body between approximately 50–1000 parts of glucose to 1 part of oxygen to a new ratio in which a slight stoichiometric excess of oxygen exists in the hydrophilic layer. Consequently, the electrode assembly is not stoichiometrically limited by the concentration of oxygen in bodily fluids, and the system operates in a manner that is sensitive to the glucose concentration being measured.

The following example is given to aid in understanding the invention, but it is to be understood that the invention is not limited to the particular materials or procedures of the example.

EXAMPLE I

A membrane-covered cylindrical oxygen sensor was fashioned from two platinum wires and a silver wire cemented into a glass bead and coated with a hydrophobic polymer. The opposite wire ends protruding through the glass bead were connected to the electrochemical analysis instrumentation. The exposed flat end of the oxygen sensor was rendered electro-chemically inactive by the application of a thin impermeable coating. A segment of silicone rubber tubing, 0.07 in. I.D.×0.11 in. O.D., (Dow Corning Corporation) was fitted over the sensor and cemented to the glass bead at the closed end leaving a concentric cavity. The enzymes were immobilized in a gel formed in the cylindrical cavity between the sensor and the tube. The gel contained 20gm % denatured bovine achilles tendon collagen, 6gm % glucose oxidase from *A. niger* (Sigma Chemical Company, type VII), and catalase. These gel components were dissolved in 0.1M phosphate buffer, pH 7.3, and cross-linked with glutaraldehyde (25% solution).

The resulting glucose sensor was placed in a sealed, thermostated (37° C.) vessel containing 0.1M phosphate buffer, pH 7.3, and equilibrated with the gas mixture containing 1.8% oxygen (0.02mM).

An identical oxygen sensor without the enzyme was used to indicate the ambient oxygen concentration. Aliquots of concentrated glucose were added and the following results obtained:

TABLE 1
Sensor Response to Glucose

| | | | | | | |
|---|---|---|---|---|---|---|
| Glucose Concentration (mM) | 0.0 | 0.25 | 0.50 | 1.00 | 4.00 | 8.50 |
| Sensor Signal (%) (Glucose electrode signal normalized by oxygen reference electrode signal) | 0 | 48 | 54 | 62 | 75 | 95 |

We claim:
1. A sensor system for determining the concentration of a predetermined first material in a body fluid, which first material reacts stoichiometrically in said body fluid in the presence of a catalyst or enzyme with a second material to form a third material, which system comprises:
   first sensor means and second sensor means, each having a surface sensitive to either said second material or said third material and each producing a signal indicative of the concentration of said second or third material in said body fluid in contact with said surface of said sensor means;
   a first permeable layer disposed completely across the surface of said first sensor means and containing said catalyst or enzyme, said first layer being permeable to all of said first, second and third materials;
   a like first permeable layer disposed completely across the surface of said second sensor means but not containing said catalyst or enzyme;
   a second permeable layer disposed completely across each of said first layers distal to said surface of said sensor means, said second layer being permeable to said second material but substantially impermeable to said first material;
   the disposition of said first and second layers thus permitting said second material to enter said layers for migration to said sensor means through the periphery of both of said layers and the distal surface of said second layer but essentially permitting like entry of said first material only through the periphery of said first layer; and
   means to compare said signals to determine the concentration of said first material in said body fluid.

2. A sensor system as in claim 1 wherein said second material is oxygen and said third material is hydrogen peroxide and said first and second sensor means are sensitive to the concentration of one of said materials.

3. A sensor system as in claim 1 wherein said first layer is permeable to glucose and oxygen.

4. A sensor system as in claim 1 wherein said second layer is permeable to oxygen and substantially impermeable to glucose.

5. A sensor system as in claim 1 wherein said first material to which said first layer is permeable is selected from the group consisting of glucose, lactates, amino acids and alcohol.

6. A sensor system as in claim 1 wherein said second material to which both layers are permeable is oxygen and said third material to which said first layer is permeable is hydrogen peroxide.

7. A sensor system as in claim 1 wherein said enzyme is glucose oxidase or catalase.

8. A sensor system as in claim 1 wherein said first layer is comprised of polyacrylamide, glutaraldehyde-cross-linked collagen or albumen, polyhydroxyethyl methacrylate and its derivatives and other hydrophilic proteins, polymers and copolymers.

9. A sensor system as in claim 1 wherein said second layer is comprised of polydimethylsiloxane, polymers of tetrafluoroethylene or its fluoro-chloro analogs alone or as copolymers with ethylene or propylene, polyethylene, polypropylene, cellulose acetate and other oxygen-imbibing hydrophobic polymeric materials.

10. A method for determining the concentration of a predetermined first material in a body fluid, which comprises:
   (a) placing in said body fluid a sensor system comprising first and second sensor means, each having a surface sensitive to either a second or third material in said body fluid, a first permeable layer disposed completely across the surface of both said sensor means and a second permeable layer disposed completely across said first permeable layer distal to said sensor means surface, said first layer being permeable to all of said first, second and third materials and said second layer being permeable to said second material and substantially impermeable to said first material, with said first layer disposed across the surface of said first sensor means having contained therein a catalyst or enzyme in whose presence said first material will react stoichiometrically with said second material to form said third material;
   (b) passing a quantity of said body fluid through the periphery of said layers and the surface of said second layer distal to said sensor means, that portion of said fluid passing through the periphery of said first layer containing both said first and second materials and the remaining portion of said quantity of body fluid containing only said second material;
   (c) for that portion of said body fluid passing through said first layer to said surface of said second sensor means, generating from said second sensor means a first signal indicative of the concentration of said second or third material in said body fluid;
   (d) in that portion of said body fluid passing through said first layer to said first sensor means, stoichiometrically reacting said first and second materials in the presence of said catalyst or enzyme to form said third material, conveying unreacted second material and said third material to said surface of said first sensor means, and from said first sensor means generating a second signal indicative of the concentration of said second or third material in said body fluid following said reaction; and
   (e) comparing said signals to determine the concentration of said first material in said body fluid.

11. A method as in claim 10 wherein said first layer comprises polyacrylamide, glutaraldehyde-cross-linked collagen or albumen, polyhydroxyethyl methacrylate and its derivatives and other hydrophilic proteins, polymers and copolymers.

12. A method as in claim 10 wherein said second layer comprises polydimethylsiloxane, polymers of tetrafluoroethylene or its fluoro-chloro analogs alone or as copolymers with ethylene or propylene, polyethylene, polypropylene, cellulose acetate and other oxygen-imbibing hydrophobic polymeric materials.

13. An improvement as in claim 12 which is conducted in vivo.

14. A method as in claim 10 which is conducted in vivo.

15. A method as in claim 10 wherein said first material is selected from the group consisting of glucose, lactate, amino acids and alcohol.

16. A method as in claim 10 wherein said second material is oxygen and said third material is hydrogen peroxide.

17. A method as in claim 10 wherein said enzyme is selected from the group consisting of glucose oxydase or catalase.

18. In a method for determining the concentration of a first material in a body fluid, which first material reacts stoichiometrically in the presence of a catalyst or enzyme with a second material to form a third material, and wherein a pair of sensors each having a sensitive surface in contact with said fluid differentially determines the concentration of said second or third material in said body fluid with and without said reaction occurring, and said concentrations are compared to indicate the concentration of said first material in said body fluid, the improvement which comprises:
   (a) forming a first permeable layer completely covering the surface of each of said sensors in said pair and a second permeable layer completely covering said first layer distal to said sensor surface; said first layer being permeable to all of said first, second and third materials and said second layer being permeable to said second material and substantially impermeable to said first material;
   (b) incorporating said catalyst or enzyme in that portion of said first layer which is disposed across the surface of one of said sensors; and
   (c) causing said second material to enter said layers with said body fluid around the periphery of both layers and at the surface of said second layer distal to said sensors, and said first material to enter only said first layer and only through the periphery thereof for reaction within said second material in the presence of said catalyst or enzyme.

19. The improvement of claim 18 wherein said first layer is permeable to glucose and oxygen.

20. The improvement of claim 18 wherein said second layer is permeable to oxygen and relatively impermeable to glucose.

21. The improvement of claim 18 wherein said surfaces are sensitive to oxygen or hydrogen peroxide.

22. An improvement as in claim 18 wherein said first material is selected from the group consisting of glucose, lactates, amino acids and alcohol.

23. An improvement as in claim 18 wherein said second material is oxygen and said third material is hydrogen peroxide.

24. An improvement as in claim 18 wherein said enzyme is glucose oxydase.

25. An improvement as in claim 18 wherein said enzyme is catalase.

* * * * *